United States Patent [19]

Vecchietti et al.

[11] Patent Number: 4,753,952
[45] Date of Patent: Jun. 28, 1988

[54] 2-ACYL-3-AMINOMETHYL-1,2,3,4-TETRAHYDROQUINOLINES

[75] Inventors: Vittorio Vecchietti; Massimo Signorini, both of Milan, Italy

[73] Assignee: Dr. Lo. Zambeletti S.p.A., Italy

[21] Appl. No.: 944,931

[22] Filed: Dec. 22, 1986

[30] Foreign Application Priority Data

Dec. 23, 1985 [GB] United Kingdom ............... 8531615

[51] Int. Cl.$^4$ ............... A61K 31/47; C07D 401/06; C07D 217/16
[52] U.S. Cl. ............................. 514/307; 514/212; 540/597; 546/145; 546/146; 546/147
[58] Field of Search ............... 546/145, 146, 147; 514/307, 212; 540/597

[56] References Cited

U.S. PATENT DOCUMENTS 3,836,536 9/1974 Morrison et al. ............... 546/147
4,565,819 1/1986 Vincent ............... 546/146

FOREIGN PATENT DOCUMENTS 1209668 10/1970 United Kingdom .
1209669 10/1970 United Kingdom .
1511463 5/1978 United Kingdom .

OTHER PUBLICATIONS

Yamashita, et al., "Chemical Abstracts," vol. 99, 1983, col. 99:23015g.

Primary Examiner—Glennon H. Hollrah
Assistant Examiner—James H. Turnipseed
Attorney, Agent, or Firm—Jacobs & Jacobs

[57] ABSTRACT

A compound of formula I:

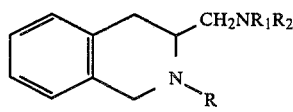

or a solvate or salt thereof in which:
R is an acyl group containing a substituted or unsubstituted carbocyclic or heterocyclic aromatic ring and $R_1$ and $R_2$ are independently $C_{1-6}$ alkyl groups or together form a $C_{3-6}$ polymethylene or alkenylene group, is useful for treating pain in mammals.

11 Claims, No Drawings

2-ACYL-3-AMINOMETHYL-1,2,3,4-TETRAHYDROQUINOLINES

This invention is concerned with novel isoquinoline derivatives, processes for their preparation, and their use in medicine, particularly as analgesics.

Compounds which are K-receptor agonists act as analgesics through interaction with Kappa opioid receptors. The advantage of K-receptor agonists over the classical μ-receptor agonists, such as morphine, lies in their ability of causing analgesia while being devoid of morphine-like behavioural effects and addiction liability.

We have now discovered a novel class of compounds which exhibit K-receptor agonism without the behavioural effects of morphine and morphine analogues, and which are thus of potential therapeutic utility as analgesics.

According to the present invention there is provided a compound, or a solvate or salt thereof, of formula I:

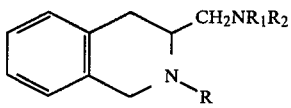
I in which:

R is an acyl group containing a substituted or unsubstituted carbocyclic or heterocyclic aromatic ring and $R_1$ and $R_2$ are independently $C_{1-6}$ alkyl groups or together form a $C_{3-6}$ polymethylene or alkenylene group. When $R_1$ and $R_2$ are $C_{1-6}$ alkyl groups, examples are methyl, ethyl, propyl, butyl, pentyl or hexyl groups, preferably methyl.

When $R_1$ and $R_2$ are polymethylene groups, examples are propylene, butylene, pentylene or hexylene, preferably butylene. As an alkenylene group, $R_1$-$R_2$ may be typically $-CH_2-CH=CH-CH_2-$.

The group R preferably has the formula II $$-CO-(CH_2)_n-X-Ar-(R_3)_m \qquad II$$

in which
n is 0, 1 or 2,
m is 0, 1 or 2,
X is a direct bond, or O, S or $NR_4$ in which $R_4$ is hydrogen or $C_{1-6}$ alkyl,
Ar is a substituted or unsubstituted carbocyclic or heterocyclic ring, and
$R_3$ is an electron withdrawing substituent, $C_{1-6}$ alkoxy, $C_{1-6}$ alkyl, aryl, or halogen.

Examples of $R^3$ are $-NO_2$, $-CN$, $-CF_3$, $-COOR_5$, $-CONR_6R_7$, $-SO_3R_8$, $-SO_2NR_9R_{10}$ and $-COR_{11}$, in which each of $R_5$ to $R_{11}$ is independently hydrogen, $C_{1-6}$ alkyl or aryl.

Suitably, $R^3$ is halogen, such as chloro or fluoro, $C_{1-6}$ alkoxy, $C_{1-6}$ alkyl, or aryl.

Typically Ar is phenyl or 2- or 3-thienyl and may be substituted by one or more halogens, typically chlorine.

X is typically oxygen or a direct bond, and n is typically 0 or 1.

Suitable examples of R are:

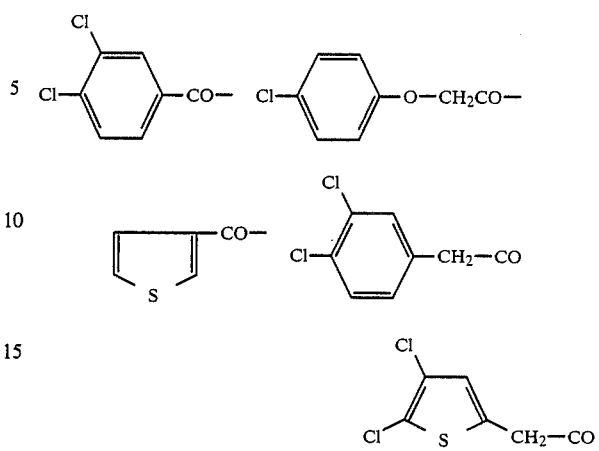

The compounds of formula I or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula I or its salt or solvate.

One preferred pharmaceutically acceptable form is the crystalline form, including such form in a pharmaceutical composition. In the case of salts and solvates the additional ionic and solvent moieties must also be non-toxic.

Examples of a pharmaceutically acceptable salt of a compound of formula I include the acid addition salts with the conventional pharmaceutical acids, for example, maleic, hydrochloric, hydrobromic, phosphoric, acetic, fumaric salicylic, citric, lactic, mandelic, tartaric, succinic, benzoic, ascorbic and methanesulphonic.

Examples of a pharmaceutically acceptable solvate of a compound of formula I include the hydrate.

The compounds of formula I have at least one asymmetric centre and therefore exist in more than one stereoisomeric form. The invention extends to all such forms and to mixtures thereof, including racemates.

The present invention also provides a process for the preparation of a compound of formula I which comprises reacting a compound of formula III

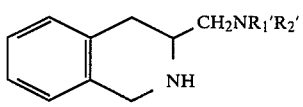
III in which $R_1'$ and $R_2'$ are $R_1$ and $R_2$ as defined for formula I or a group or atom convertible to $R_1$ and $R_2$, with a compound of formula R'—OH or an active derivative thereof, in which R' is R as defined for formula I or a group convertible to R, to form a compound of formula Ia

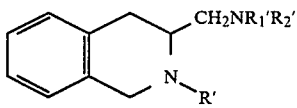

and then performing one or more of the following steps:
(a) where R', R$_1$' or R$_2$' are other than R, R$_1$ and R$_2$, converting R', R$_1$' or R$_2$' to R, R$_1$ or R$_2$ to obtain a compound of formula I,
(b) where R', R$_1$' and R$_2$' are R, R$_1$ and R$_2$, converting one R, R$_1$ or R$_2$ to another R, R$_1$ or R$_2$ to obtain a compound of formula I,
(c) forming a salt and/or solvate of the obtained compound of formula I.

Suitable active derivatives of R'—OH are acid chlorides or acid anhydrides. Another suitable derivative is a mixed anhydride formed between the acid and an alkyl chloroformate.

For example, in standard methods well known to those skilled in the art, the compound of formula III may be coupled:
(a) with an acid chloride in the presence of an inorganic or organic base,
(b) with the acid in the presence of dicyclohexyl carbodiimide, N-dimethylaminopropyl-N'-ethyl carbodiimide or carbonyl diimidazole,
(c) with a mixed anhydride generated in situ from the acid and an alkyl (for example ethyl)chloroformate.

It will be appreciated that a compound of formula Ia may be converted to a compound of formula I, or one compound of formula I may be converted to another compound of formula I, by interconversion of suitable substituents. Thus certain compounds of formula I and Ia are useful intermediates in forming other compounds of the present invention.

R$_1$' and R$_2$' may be alkyl groups and converted to R$_1$'/R$_2$' hydrogen atoms by conventional amine dealkylation. When R$_1$' or R$_2$' is benzyl or substituted benzyl it may be converted to an R$_1$ or R$_2$' hydrogen atom by catalytic hydrogenation or other method of reduction. R$_1$' and R$_2$' as hydrogen atoms may be converted to R$_1$ and R$_2$ alkyl groups by conventional amine alkylation. R$_1$' and R$_2$' are preferably R$_1$ and R$_2$ respectively.

The compound R'—OH is typically of the formula IIa

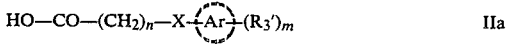

in which R$_3$' is R$_3$ as defined for formula II or a group of atom convertible to R$_3$, the other variables being as defined for formula II.

Conversions of substituents R$_3$' on the aromatic group Ar to obtain R$_3$ are generally known in the art of aromatic chemistry. R$_3$' is preferably R$_3$.

The compounds of formula I may be converted into their pharmaceutically acceptable acid addition salts by reaction with the appropriate organic or mineral acids.

Solvates of the compounds of formula I may be formed by crystallization or recrystallization from the appropriate solvent. For example hydrates may be formed by crystallization or recrystallization from aqueous solutions, or solutions in organic solvents containing water.

Also salts or solvates of the compounds of formula I which are not pharmaceutically acceptable may be useful as intermediates in the production of pharmaceutically acceptable salts or solvates. Accordingly such salts or solvates also form part of this invention.

The compounds of formula I exist in more than one stereoisomeric form and the processes of the invention produces mixtures thereof. The individual isomers may be separated one from another by resolution using an optically active acid such as tartaric acid. Alternatively, an asymmetric synthesis would offer a route to the individual form.

The compound of formula III may be prepared from 1,2,3,4-tetrahydroisoquinoline-3-carboxylic acid of formula IV by the reaction scheme shown:

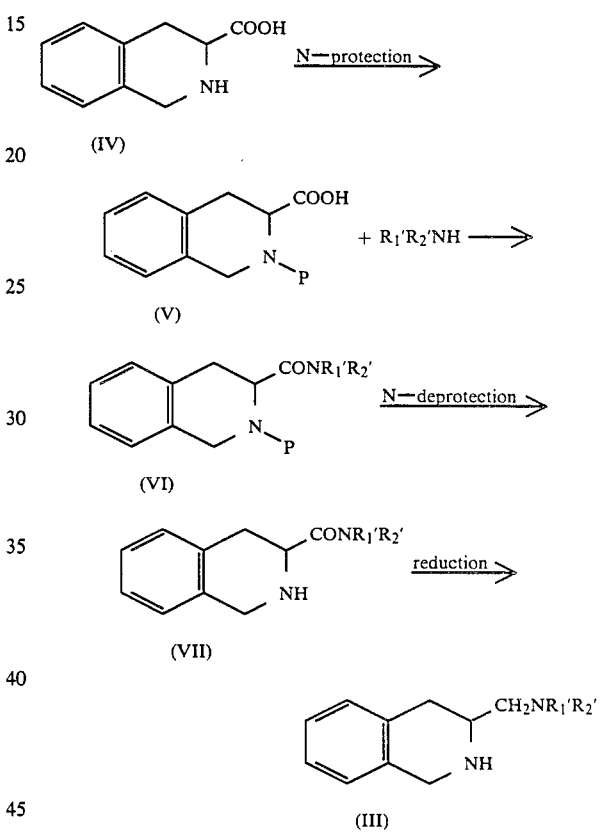

In this scheme, firstly the compound of formula IV is nitrogen protected with a conventional protecting group P, such as benzyloxycarbonyl or tert-butyloxycarbonyl, forming the compound of formula V which is reacted with the amine R$_1$'R$_2$'NH (in which R$_1$' and R$_2$' are as defined earlier) to obtain N-protected amide VI. This is conventionally N-deprotected, for example by catalytic debenzylation if P is benzyloxycarbonyl or by acid treatment if P is tert-butyloxycarbonyl, and the resulting basic amide VII is reduced to the diamine III by reaction with lithium aluminium hydride.

Alternatively, the N-protected acid V is reduced to a primary alcohol which is esterified, for example with methane sulfonic acid or p-toluenesulfonic acid, and the ester reacted with R$_1$'R$_2$'NH. Deprotection of the ring nitrogen gives the diamine III.

When the starting material of formula IV is a racemic mixture, the resulting compounds of formulae III and I are also racemic. Using a compound of formula IV in the R- or S-configuration results in the corresponding optically active products.

The compound of formula IV may be prepared by reacting phenylalanine with 37% formalin in concentrated hydrochloric acid as described by Hayashi et al (Chem. Pharm. Bull. 31, 312, 1983). Depending on the starting material (R-, S-, or R,S-phenylalanine) the corresponding optically active or racemic compounds IV, III or I are obtained.

Certain intermediates described above are novel compounds and, together with the described processes for their preparation, they form a further aspect of this invention.

The activity of the compounds of formula I in standard analgesic tests indicates that they are of therapeutic utility in the treatment of pain.

Accordingly the present invention also provides a compound of formula I, or a pharmaceutically acceptable salt or solvate thereof, for use as an active therapeutic substance.

The present invention further provides a pharmaceutical composition comprising a compound of formula I, or a pharmaceutically acceptable salt or solvate thereof, and a pharmaceutically acceptable carrier.

The present invention also provides the use of a compound of formula I, or a pharmaceutically acceptable salt or solvate thereof, in the manufacture of a medicament for the treatment of pain.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known analgesic agents.

Preferably, a pharmaceutical composition of the invention is in unit dosage form and in a form adapted for use in the medical or veterinarial fields. For example, such preparations may be in a pack form accompanied by written or printed instructions for use as an agent in the treatment of pain.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn or a solid form or concentrate which can be used to prepare an injectable formulation.

As mentioned earlier, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

Within the above mentioned dosage ranges, no adverse toxicological effects have been observed with compounds of the invention.

The present invention also provides a method of treating pain in mammals, particularly in humans, which comprises administering an effective amount of a compound of formula I, or a pharmaceutically acceptable salt or solvate thereof, to a sufferer.

Compounds of this invention and their preparation are illustrated in the following Examples.

EXAMPLE 1

(R,S)-2-(3,4-dichlorophenyl)acetyl-3-(1-pyrrolidinyl)-methyl-1,2,3,4-tetrahydroisoquinoline hydrochloride 3.1 g of 3,4-dichlorophenylacetylchloride (0.0139 moles) dissolved in 10 ml of chloroform, were added dropwise to a stirred solution of 3.6 g of (R,S)-3-(1-pyrrolidinyl)methyl-1,2,3,4-tetrahydrosisoquinoline (0.01244 moles) and 7 ml of triethylamine (0.05 moles) in 100 ml of chloroform. The mixture was left overnight at room temperature, and subsequently washed with water, diluted sodium hydroxide and sodium chloride solution. The chloroform solution was evaporated to dryness in vacuo, the residue dissolved in aqueous citric acid, and the resulting solution washed with ether.

The acid solution was made alkaline with diluted sodium hydroxide, and the precipitate extracted with dichloromethane. After evaporating to dryness in vacuo, the residue was purified by silica gel chromatography, eluting with chloroform/methanol 99/1. The purified base (1.6 g) was dissolved in acetone and the solution brought to acidic pH with HCl saturated ether. The crystalline precipitate (yield 1.5 g) was filtered, washed with ether and dried.

| NMR (CDCl$_3$-90 MHz) | | |
|---|---|---|
| δ = 1.80–2.45 | m | 4H |
| 2.50–3.40 | m | 6H |
| 3.55–4.20 | m | 2H |
| 3.95 | AB system J = 15.75 | 2H |
| 4.95 | AB system J = 17.25 | 2H |
| 5.30–5.65 | m | 1H |
| 7.0–7.5 | m | 7H |
| 11.75 | broad s | 1H |

By the same procedure, the following compounds were prepared from the appropriate amine and 3,4-dichlorophenylacetylchloride, and the compounds are summarised in Table 1.

EXAMPLE 2

(R)-2-(3,4-dichlorophenyl)acetyl-3-(1-pyrrolidinyl)-methyl-1-2,3,4-tetrahydroisoquinoline hydrochloride

| NMR (CDCl$_3$-90 MHz) | | |
|---|---|---|
| δ = 1.80–2.45 | m | 4H |
| 2.50–3.40 | m | 6H |
| 3.55–4.20 | m | 2H |
| 3.95 | AB system J = 15.75 | 2H |
| 4.95 | AB system J = 17.25 | 2H |
| 5.30–5.65 | m | 1H |
| 7.0–7.5 | m | 7H |
| 11.75 | broad s | 1H |

EXAMPLE 3

(S)-2-(3,4-dichlorophenyl)acetyl-3-(1-pyrrolidinyl)-methyl-1,2,3,4-tetrahydroisoquinoline hydrochloride

| NMR (CDCl$_3$-90 MHz) | | |
|---|---|---|
| δ = 1.80–2.45 | m | 4H |
| 2.50–3.40 | m | 6H |
| 3.55–4.20 | m | 2H |
| 3.95 | AB system J = 15.75 | 2H |
| 4.95 | AB system J = 17.25 | 2H |
| 5.30–5.65 | m | 1H |
| 7.0–7.5 | m | 7H |
| 11.75 | broad s | 1H |

EXAMPLE 4

(R,S)-2-(3,4-dichlorophenylacetyl)-3-dimethylaminomethyl-1,2,3,4-tetrahydroisoquinoline hydrochloride.

| NMR (CDCl$_3$-300 MHz) | | |
|---|---|---|
| δ = 2.70–2.85 | m | 2H |
| 2.80 | d J = 5 | 3H |
| 3.0 | d J = 5 | 3H |
| 3.2 | m | 2H |
| 4.05 | AB system J = 15 | 2H |
| 5.05 | AB system J = 16.8 | 2H |
| 5.5 | m | 1H |
| 7.15–7.55 | m | 7H |
| 12.2 | broad s | 1H |

EXAMPLE 5

(R)-2-(3,4-dichlorophenyl)acetyl-3-dimethylaminomethyl-1,2,3,4-tetrahydroisoquinoline hydrochloride

| NMR (CDCl$_3$-300 MHz) | | |
|---|---|---|
| δ = 2.70–2.85 | m | 2H |
| 2.80 | d J = 5 | 3H |
| 3.0 | d J = 5 | 3H |
| 3.2 | m | 2H |
| 4.05 | AB system J = 15 | 2H |
| 5.05 | AB system J = 16.8 | 2H |
| 5.5 | m | 1H |
| 7.15–7.55 | m | 7H |
| 12.2 | broad s | 1H |

EXAMPLE 6

(S)-2-(3,4-dichlorophenylacetyl)-3-dimethylaminomethyl-1,2,3,4-tetrahydroisoquinoline hydrochloride

| NMR (CDCl$_3$-300 MHz) | | |
|---|---|---|
| δ = 2.70–2.85 | m | 2H |
| 2.80 | d J = 5 | 3H |
| 3.0 | d J = 5 | 3H |
| 3.2 | m | 2H |
| 4.05 | AB system J = 15 | 2H |
| 5.05 | AB system J = 16.8 | 2H |
| 5.5 | m | 1H |
| 7.15–7.55 | m | 7H |
| 12.2 | broad s | 1H |

TABLE 1

General Formula

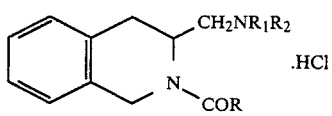

| EXAMPLE NO. | R | R₁ | R₂ | Stereochemistry at Carbon 3 | Molecular formula | Molecular Weight | Melting Point (°C.) | $[\alpha]_D$ |
|---|---|---|---|---|---|---|---|---|
| 1 | $-CH_2-\text{(2,4-Cl}_2\text{-C}_6\text{H}_3)$ | $R_1R_2 =$ cyclopropyl | | R,S | $C_{22}H_{24}Cl_2N_2O \cdot HCl$ | 439.807 | 228–30 | — |
| 2 | " | " | | R | " | " | 218–20 | −32.3 (c = 1 MeOH) |
| 3 | " | " | | S | " | " | 217–18 | +32.3° (c = 2 MeOH) |
| 4 | " | $-CH_3$ | $-CH_3$ | R,S | $C_{20}H_{22}Cl_2N_2O \cdot HCl$ | 413.771 | 247–9 | — |
| 5 | " | " | " | R | " | " | 240–2 | −25 (c = 1 MeOH) |
| 6 | " | " | " | S | " | " | 247–8 | +21.4° (c = 1 MeOH) |

The pharmacological activity of the compounds of this invention is illustrated by various relevant in vitro and in vivo animal models, using the classical μ-agonist morphine as a reference standard.

Inhibition of contraction in electrically stimulated rabbit vas deferens indicate Kappa receptor agonism. The mouse p-phenylquinone writhing test and mouse tail flick test demonstrate analgesic activity, while the latter test also allows observation of behavioural effects typical of morphine and its analogues (Straub tail in the mouse) and K-agonists (reduced locomotor activity).

The test procedures for illustrative compounds are as follows; and the results are shown in Table 2.

PHARMACOLOGICAL PROCEDURES

Rabbit vas deferens (According to Oka et al., Eur. J. Pharm. 73, 235/1980) White New Zealand male rabbits weighing 3.5–4 Kg are used. The animals are killed by cervical dislocation and exanguinated. The abdomen is open by a medial incision, the vas is gently cleared of the membrane and blood vessels surrounding it and any seminiferous fluid remaining in the vas is removed; the vas is placed in warm Krebs solution of the following composition (mM): NaCl 118; KCl 4.75; $CaCl_2$ 2.57; $KH_2PO_4$ 0.95; $NaHCO_3$ 25; glucose 11. The isolated vas is divided in three equal portions, the prostatic, middle and epididymal. Only the prostatic and middle portions of the vas are used because they were found to be the most sensitive to K-receptor agonists while the epididymal portion was less sensitive. The vas is then suspended in a 20 ml organ bath containing the same solution aforementioned, kept at 37° C. by means of water jacket and gassed with 95% $O_2$ and 5% $CO_2$. The initial resting tension is adjusted to 500 mg. Developed tension is recorded via an isometric transducer on ink writting Battaglia-Rangoni recorder, Mod. 7050. The intramural nerves are stimulated through two platinum electrodes with supramaximal rectangular pulses of 1 msec duration 0.1 Hz. After 30 min of stabilization, drugs are added to the medium bathing the tissue and left in contact for 20 minutes. Cumulative dosing are always used.

Results are expressed as percent reduction of maximal developed tension.

Writhing test (According to Siegmund et al., Proc. Soc. Exptl. Biol. 95, 729/1957)

Male Charles River mice, average weight 26 g, are randomly distributed into groups of 10 and are dosed subcutaneously with compounds under test, dissolved in isotonic saline (20 ml.Kg⁻¹). The experiments are carried out in the presence of positive and negative controls. 20 min after the mice are injected intraperitoneally with p-phenylquinone 0.02%, 10 ml.Kg⁻¹, maintained at 37° C. in a water bath. The mice are placed in a perspex compartmented observation box and observed for a period of 8 min after injection of p-phenylquinone. The dose-response curve is obtained by basing observation on the all or none response.

Analgesic activity is calculated as percentage of animals completely protected from writhing in an 8 min period:

$$\% \text{ analgesia} = \frac{\text{No. of mice failing to writhe}}{\text{Total no. of mice per group}} \times 100$$

Tail-flick test (Modified from the procedure published by D'Amour et al., J. Pharm. Exptl. Ther. 72, 74/1941)

Male Charles River mice, average weight 26 g, are used. Selection is carried out before beginning of experiments: only mice whose reaction time is less than 8 sec are used. They are randomly distributed into groups of 10 and dosed with compounds under test, with positive and negative controls being included.

Compounds under test are administered subcutaneously in isotonic saline in a volume of 20 ml.Kg⁻¹. 30 min later mice are placed again under heat source (Socrel apparatus) and reaction time is recorded.

Analgesic activity of the test compound is expressed as the percent number of mice doubling the initial time within a group.

$$\% \text{ analgesia} = \frac{\text{No. of mice doubling the reaction time}}{\text{Total no. of mice per group}} \times 100$$

RECEPTOR AFFINITY STUDY

Tissue Preparation

Radio receptor binding to μ and k sites is performed on fresh guinea pig brain homogenate prepared according to Kosterlitz. (1981)

While brain without cerebellum is homogenized in 50 mM, Tris-buffer (pH 7.4 at 0° C.) and centrifuged at 49,000×g×10 min. The pellet is then resuspended in the same buffer, incubated at 37° C. for 45 min. and centrifuged again.

1.9 ml of the final homogenate (1:100 in Tris-pH 7.4, 0° C.) is used for the binding assay.

Binding to μ sites (Magnan J., 1982):

$^3$H [D-Ala$^2$, MePhe$^4$, Gly-ol$^5$] Enkephalin ($^3$H-DAGO), an enkephalin analogue that binds selectively to μ receptor, is added to the biological substrate and incubated at 25° C. for 40 min., filtered through Whatman GF-C and washed with ice-cold Tris-buffer. The filters are then dried, solubilized in Filtercount and the radioactivity monitored. Non specific binding is determined in the presence of $10^{-6}$M Naloxone.

Binding to K sites (Magnan J., 1982):

The binding of tritiated Ethylketocyclazocine to brain homogenate is measured in the presence of 100 nanomolar D-Ala-D-LeuEnkephalin (DADLE) and 100 nanomolar DAGO, added to saturate the δ and μ opioid receptors respectively.

Final homogenate with solutions of the cold ligand and of the labelled ligand is incubated for 40 min at 25° C., filtered through Whatman GF/C glass filter discs and washed.

The radioactivity bound to the filters is counted by liquid scintillation spectrophotometry.

MR 2266,500 nM is utilized to determine the saturable binding.

For the calculation of the kinetic parameters of the binding of labelled and unlabelled ligands, the equilibrium dissociation constant ($K_D$), and the inhibition constant (Ki) and the maximum number of binding sites (B max) are determined from saturation curves and competition experiments (Hill 1910; Scatchard 1949; Cheng and Prusoff 1973; Gillan et al. 1980).

A concentration of radioligant near $K_D$ is used in the binding assays evaluating our compounds.

| Hill, A. V. (1910) | J. Physiol. 40. IV–VIII (1910) |
| Scatchard G. (1949) | Ann. N.Y. Acad. Sci., 51, 660–674 |
| Cheng and Prusoff W. H. (1973) | Biochem. Pharmac. 22, 3099–3102 |
| Gillan M. G. C., Kosterlitz H. W. and Paterson S. Y. (1980) | Br. J. Pharmac. 70, 481–490 |
| Kosterlitz H. W. Paterson S. Y. and Robson L. E. (1981) | Br. J. Pharmac. 73, 939–949 |
| Magnan J., Paterson S. Y., Tavani A., and Kosterlitz H. W. (1982) | Arch. Pharmacol. 319, 197–205 |

TABLE 2

| Example No. | IN VIVO TESTS - ED$_{50}$ mg · Kg$^{-1}$s.c. | | RECEPTOR BINDING -Ki(nM) | |
|---|---|---|---|---|
| | Mouse tail flick | Mouse p-phenylquinone writhing | μ | k |
| 1 | 3.12 | 2.64 | 960 | 9.45 |
| 2 | N.E. | N.E. | 1416 | >1.000 |
| 3 | 1.58 | 1.43 | 764 | 8.03 |
| 4 | 7.2 | 3.76 | 1359 | 17.49 |
| 5 | N.E. | N.E. | 2561 | 637 |
| 6 | 1.65 | 2.05 | 1077 | 10.96 |

What is claimed is:

1. A compound of formula I:

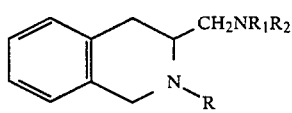

or a solvate or pharmaceutically acceptable salt thereof in which R has the formula (II):

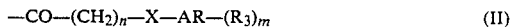

in which n is 0, 1 or 2, m is 0, 1 or 2,

X is a direct bond, or O, S or NR$_4$ in which R$_4$ is hydrogen or C$_{1-6}$ alkyl, Ar is phenyl or thienyl, and R$_3$ is an electron withdrawing substituent, C$_{1-6}$ alkoxy, C$_{1-6}$ alkyl, phenyl; and R$_1$ and R$_2$ are independently C$_{1-6}$ alkyl groups or together form a C$_{3-6}$ polymethylene or C$_{3-6}$ alkenylene group.

2. A compound according to claim 1, in which each of R$_1$ and R$_2$ is methyl, ethyl, propyl, butyl, pentyl, or hexyl.

3. A compound according to claim 1, in which R$_1$ and R$_2$ together form a propylene, pentylene or hexylene group, or a —CH$_2$—CH=CH—CH$_2$— group.

4. A compound according to claim 1, in which R$_1$ and R$_2$ together form a butylene group.

5. A compound according to claim 1, in which R$_3$ is —NO$_2$, —CN, —CF$_3$, —COOR$_5$, —CONR$_6$R$_7$, SO$_3$R$_8$, —SO$_2$NR$_9$R$_{10}$ and —COR$_{11}$, in which each of R$_5$ to R$_{11}$ is independently hydrogen, C$_{1-6}$ alkyl or phenyl.

6. A compound according to claim 1, in which R$_3$ is chloro, fluoro, C$_{1-6}$ alkoxy, C$_{1-6}$ alkyl, or phenyl.

7. A compound according to claim 1, in which Ar is phenyl or 2- or 3-thienyl.

8. A compound selected from:

(R,S)-2-(3,4-dichlorophenyl)acetyl-3-(1-pyrrolidinyl)methyl-1,2,3,4-tetrahydroisoquinoline hydrochloride, (R)-2-(3,4-dichlorophenyl)acetyl-3-(1-pyrrolidinyl)-methyl-1,2,3,4-tetrahydroisoquinoline hydrochloride, (S)-2-(3,4-dichlorophenyl)acetyl-3-(1-pyrrolidinyl)-methyl-1,2,3,4-tetrahydroisoquinoline hydrochloride, (R,S)-2-(3,4-dichlorophenylacetyl)-3-dimethylaminomethyl-1,2,3,4-tetrahydroisoquinoline hydrochloride, (R)-2-(3,4-dichlorophenyl)acetyl-3-dimethylaminomethyl-1,2,3,4-tetrahydroisoquinoline hydrochloride, (S)-2-(3,4-dichlorophenylacetyl)-3-dimethylaminomethyl-1,2,3,4-tetrahydroisoquinoline hydrochloride.

9. a pharmaceutical composition for treating pain in mammals, comprising an effective amount of a compound according to claim 1, and a pharmaceutically acceptable carrier.

10. A composition according to claim 9 in unit dosage form.

11. A method of treating pain in mammals which comprises administering an effective, non-toxic amount of a compound according to claim 1 to a sufferer.

* * * * *